(12) United States Patent
Antenucci

(10) Patent No.: US 9,266,800 B2
(45) Date of Patent: Feb. 23, 2016

(54) STABLE COMPOSITIONS OF TRIFLUOROETHYLENE

(71) Applicant: SOLVAY SPECIALTY POLYMERS ITALY S.P.A., Bollate (IT)

(72) Inventor: Emanuela Antenucci, Saronno (IT)

(73) Assignee: SOLVAY SPECIALTY POLYMERS ITALY S.P.A., Bollate (Milano) (IT)

(*) Notice: Subject to any disclaimer, the term of this patent is extended or adjusted under 35 U.S.C. 154(b) by 33 days.

(21) Appl. No.: 14/376,043

(22) PCT Filed: Jan. 31, 2013

(86) PCT No.: PCT/EP2013/051852
§ 371 (c)(1),
(2) Date: Jul. 31, 2014

(87) PCT Pub. No.: WO2013/113785
PCT Pub. Date: Aug. 8, 2013

(65) Prior Publication Data
US 2015/0017064 A1    Jan. 15, 2015

(30) Foreign Application Priority Data

Feb. 2, 2012 (EP) .................................. 12153604

(51) Int. Cl.
*C07C 17/354* (2006.01)
*C07C 17/04* (2006.01)
*C07C 17/42* (2006.01)
*C07C 17/23* (2006.01)
*C07C 21/18* (2006.01)

(52) U.S. Cl.
CPC ............. *C07C 17/42* (2013.01); *C07C 17/23* (2013.01); *C07C 17/354* (2013.01); *C07C 21/18* (2013.01); *C07C 17/04* (2013.01); *Y10T 428/13* (2015.01)

(58) Field of Classification Search
CPC ............................... C07C 17/354; C07C 17/04
USPC .................................................... 570/175, 124
See application file for complete search history.

(56) References Cited

FOREIGN PATENT DOCUMENTS

| EP | 459463 A1 | 12/1991 |
|---|---|---|
| GB | 619758 A1 | 3/1949 |
| WO | 201200853 A1 | 1/2012 |

OTHER PUBLICATIONS

Feiring A.E. et al., "Trifluoroethylene deflagration" Chemical & Engineering News, 1997, vol. 75, No. 51, p. 6—American Chemical Society.
Wang Z. et al., "High dielectric VDF/TrFE/CTFE terpolymers prepared by hydrogenation of VDF/CTFE copolymers: synthesis and characterization", Macromolecules, 2006, vol. 39, pp. 4268-4271—American Chemical Society.
Anonymous, "Halocarbon Material Safety Data Sheet", Halocarbon, May 23, 2005, 5 pages, XP002673763, Retrieved from the Internet: URL:http://www.halocarbon.com/halocarbon_media/Trifluoroethylene_190.pdf [retrieved on Apr. 12, 2012].

*Primary Examiner* — Elvis O Price

(57) ABSTRACT

A trifluoroethylene composition which is safe to handle and which can be safely stored and transported at pressures of up to 5.00 MPa. The composition comprises trifluoroethylene and HCl in a molar ratio trifluoroethylene:HCl from 10:90 to 63:37. When the composition is a compressed gas it has a pressure of from 0.50 to 5.00 MPa.

15 Claims, No Drawings

STABLE COMPOSITIONS OF TRIFLUOROETHYLENE

CROSS-REFERENCE TO RELATED APPLICATIONS

This application is a U.S. national stage entry under 35 U.S.C. §371 of International Application No. PCT/EP2013/051852 filed Jan. 31, 2013, which claims priority to European Application No. EP12153604.9, filed on Feb. 2, 2012. The entire contents of these applications are explicitly incorporated herein by this reference.

TECHNICAL FIELD

The present invention relates to compositions of trifluoroethylene and hydrogen chloride, in particular gaseous and liquid compositions, which are stable towards deflagration.

BACKGROUND ART

Trifluoroethylene ($CHF=CF_2$) is a known compound used as a monomer in the preparation of various fluorinated polymers. Trifluoroethylene is a gas at ambient temperature. The storage and transportation of trifluoroethylene poses a number of safety issues in view of its tendency to violently deflagrate, see for instance FEIRING, A. E., et al. Trifluoroethylene deflagration. *Chemical&Engineering News*. 1997, vol. 75, no. 51, p. 6.

Trifluoroethylene is known to disproportionate with liberation of great amounts of heat resulting in a significant pressure rise and explosion. The disproportionation reaction can be triggered by the polymerization of trifluoroethylene which occurs spontaneously. For this reason polymerization inhibitors, such as limonene, are generally added in amounts of up to 5% by weight to trifluoroethylene. However polymerization inhibitors do not render trifluoroethylene stable, they only remove a potential source of ignition. Thus, the presence of known polymerization inhibitors is not sufficient to eliminate the deflagration hazard connected with the storage and transportation of trifluoroethylene, see FEIRING, A. E., et al. Trifluoroethylene deflagration. *Chemical&Engineering News*. 1997, vol. 75, no. 51, p. 6.

Although trifluoroethylene can be liquefied by sufficient pressurization in a container, storage and transportation of trifluoroethylene as a liquid is generally avoided because of the risks of explosion of the gas in equilibrium with the liquid (the gas phase may contain not enough polymerization inhibitor because the inhibitor is less volatile than trifluoroethylene). Thus, as a precaution, liquid trifluoroethylene is generally kept below −30° C. and its quantity is kept to the minimum required for the process. On the other hand a stable gas phase in equilibrium with a liquid phase would reduce the risk of ignition of the liquid phase itself, as deflagration of the liquid is usually possible only after ignition of the gas phase.

Studies with trifluoroethylene in the gas phase indicate that there is a reduced risk of disproportionation at pressures below 0.35 MPa. As pressure increases above this value, the risk of disproportionation and, consequently, deflagration increases. For this reason trifluoroethylene is generally stored, handled and transported at pressures not exceeding 0.30 MPa. The amount of trifluoroethylene transported per unit volume is thus very limited with a great impact on the cost of this material. The safety and consequently, cost issues related to the storage and transportation of trifluoroethylene are such to limit the use of trifluoroethylene as a monomer regardless of the potential economic interest of the polymers obtainable therefrom (see for instance WANG, Z., et al. High dielectric VDF/TrFE/CTFE terpolymers prepared by hydrogenation of VDF/CTFE copolymers: synthesis and characterization. *Macromolecules*. 2006, vol. 39, p. 4268-4271.).

Thus the need exist for means of safely storing and transporting trifluoroethylene.

SUMMARY OF INVENTION

It has now been found that certain compositions of trifluoroethylene and hydrogen chloride (HCl) are stable towards deflagration even when compressed to pressures above 0.35 MPa and thus they can be safely stored, handled and transported as a liquid or as a compressed gas at a pressure of up to 5.00 MPa.

Thus a first object of the present invention is a liquid or compressed gas composition comprising trifluoroethylene and HCl in a molar ratio trifluoroethylene:HCl from 10:90 to 63:37 wherein when the composition is in the gas phase the pressure is from 0.50 to 5.00 MPa.

The molar ratio trifluoroethylene:HCl is generally equal to or greater than 20:80, preferably equal to or greater than 25:75, even equal to or greater than 30:70.

Advantageous compositions are those wherein the molar ratio trifluoroethylene:HCl is from 40:60 to 60:40. Particularly useful compositions have been found to be those wherein the molar ratio trifluoroethylene:HCl is 50:50.

Compositions wherein the molar ratio trifluoroethylene:HCl is 50:50 and below have been proven to be extremely stable over the whole range of pressures from 0.50 to 5.0 MPa even at temperatures higher than ambient temperature, e.g 45° C.

Compositions wherein the molar ratio trifluoroethylene:HCl is between 50:50 and 63:37 have been tested to be stable at least up to pressures of 1.80 MPa.

Compositions wherein the molar ratio trifluoroethylene:HCl is greater than 63:37, in particular when in the gas phase, have not shown the same stability towards deflagration as the inventive compositions.

In addition to trifluoroethylene and HCl, the inventive composition may comprise other components. Typically these additional components are selected from components that do not promote the polymerization or the disproportionation of trifluoroethylene. Said additional components may be of different nature depending on the physical state of the composition. The composition may for instance comprise 1 to 5% by weight of known polymerization inhibitors, such as limonene. Examples of additional components for compressed gas compositions of the invention are notably inert gases like nitrogen.

The composition may comprise any amount of the combined weight of trifluoroethylene and HCl in the molar ratios defined above. The composition may comprise 5, 10, 20 and even 30% by weight of the combined weight of trifluoroethylene and HCl. Trifluoroethylene and HCl typically represent at least 50% by weight of the composition. Preferably trifluoroethylene and HCl represent at least 80% by weight of the composition, more preferably at least 90% by weight of the composition, and even more preferably at least 95%. Advantageously, the combined weight of trifluoroethylene and HCl may represent 98% by weight or more of the composition. The composition may consist of trifluoroethylene and HCl without risk of deflagration.

The inventive composition is a liquid or a compressed gas. In a first embodiment the composition is a liquid. The term "liquid" is used herein to encompass also solid compositions obtained by cooling a liquid composition below its melting temperature.

The liquid composition comprises at least 20% by weight, typically at least 50% by weight of the combined weight of trifluoroethylene and HCl, preferably at least 80% by weight, more preferably at least 90% by weight, and even more preferably at least 95% by weight.

In the liquid composition the molar ratio trifluoroethylene:HCl is typically at least 10:90, preferably at least 30:70 and more preferably at least 40:60. The molar ratio trifluoroethylene:HCl is typically no more than 60:40, preferably no more than 50:50.

In an aspect of this first embodiment the liquid composition is in equilibrium with a gas phase. The vapour pressure of HCl is higher than the vapour pressure of trifluoroethylene, accordingly the gas phase in equilibrium with the liquid composition is generally richer in HCl further reducing the risk of deflagration of the liquid/gas system.

In a second embodiment of the invention the composition is a compressed gas at a pressure of from 0.50 to 5.00 MPa. Preferably, the partial pressure of trifluoroethylene does not exceed 2.50 MPa.

Compressed gas compositions having a molar ratio trifluoroethylene:HCl of 50:50 and below have been found to be stable at pressures from 0.50 MPa to 5.00 MPa, such as at a pressure greater than 0.80 MPa, greater than 1.00 MPa, greater than 1.50 MPa, greater than to 2.00 MPa, greater than 3.00 MPa, greater than 4.00 MPa.

Compressed gas compositions having a molar ratio trifluoroethylene:HCl from 50:50 to 63:37 have been tested up to 1.80 MPa and have been found to be stable up to that pressure.

The molar ratio trifluoroethylene:HCl in the compressed gas composition is equal to or greater than 10:90, generally equal to or greater than 20:80, preferably equal to or greater than 25:75, more preferably equal to or greater than 30:70, and even more preferably equal to or greater than 40:60.

Typically the compressed gas composition comprises at least 50% by weight of the combined weight of trifluoroethylene and HCl, preferably at least 80% by weight, more preferably at least 90% by weight and even more preferably at least 95% by weight. The compressed gas composition may comprise 99% by weight or more of the combined weight of trifluoroethylene and HCl; it may even advantageously consist of HCl and trifluoroethylene.

Useful compressed gas compositions are those compositions comprising at least 95% by weight, preferably 99% by weight or more of the combined weight of trifluoroethylene and HCl, having a pressure of from 0.50 to 2.00 MPa, preferably from 1.00 to 1.80 MPa, wherein the molar ratio trifluoroethylene:HCl is from 50:50 to 60:40.

Particularly advantageous compositions are those compositions comprising at least 95% by weight, preferably 99% by weight or more of the combined weight of trifluoroethylene and HCl, having a pressure of from 0.50 to 5.00 MPa, preferably from 2.00 to 5.00 MPa, wherein the molar ratio trifluoroethylene:HCl is from 40:60 to 50:50.

It can be appreciated that the compositions detailed above allow to store and transport a net amount of trifluoroethylene per unit volume which is higher than the amount that is stored and transported at present (at a pressure of 0.30 MPa), while at the same time eliminating the risks of deflagration as the inventive compositions are inherently stable over a wide range of pressures and compositions.

A second object of the present invention is a process for the preparation of the inventive composition comprising the step of compressing a gaseous composition comprising trifluoroethylene and HCl in a molar ratio from 10:90 to 63:37 to obtain a liquid or a compressed gas at a pressure from 0.50 MPa to 5.00 MPa. Preferably, the partial pressure of trifluoroethylene should not exceed 2.50 MPa at any time during the process. The process may optionally comprise the step of reducing the temperature below ambient temperature to obtain the liquid composition.

Hereinafter the expression "gaseous composition" will be intended to denote a gaseous composition comprising trifluoroethylene and HCl in a molar ratio from 10:90 to 63:37 at a pressure of less than 0.50 MPa.

Any suitable method and equipment known in the art for the compression of hazardous materials can be used to carry out the process of preparing the inventive composition.

Any process may be employed to prepare the gaseous composition to be compressed.

In one embodiment a feed of gaseous trifluoroethylene and a feed of gaseous HCl may be mixed together in the set molar ratio at a pressure of less than 0.50 MPa, typically at atmospheric pressure (0.10 MPa), and then compressed to provide the composition of the invention. Any additional component of the composition may be present in either the trifluoroethylene feed, and/or in the HCl feed or alternatively it can be mixed with the trifluoroethylene and HCl mixture after its preparation.

In another embodiment of the process the gaseous composition to be compressed is the product obtained from a gas-phase catalytic process for the preparation of trifluoroethylene. A number of gas-phase catalytic processes are known for the preparation of trifluoroethylene.

The catalytic hydrodechlorination of chlorotrifluoroethylene to prepare trifluoroethylene has been disclosed for instance in WO 2012/000853 A (SOLVAY SOLEXIS SPA) May 1, 2012. In such a process chlorotrifluoroethylene and hydrogen are reacted in the gas-phase in the presence of a heterogeneous catalyst, typically comprising palladium or platinum, to yield trifluoroethylene. HCl is also produced as a by-product of the reaction in a theoretical 50:50 molar ratio with trifluoroethylene. The effluent gas resulting from the above described process, after adequate purification to remove any unreacted chlorotrifluoroethylene, hydrogen, any inert gas optionally present in the reactant feed, as well as any by-products additionally produced in the process, can therefore be conveniently used for the preparation of the inventive composition. The effluent gas is typically in an uncompressed state as the hydrodechlorination of chlorotrifluoroethylene is generally carried out under reduced or atmospheric pressure. The molar ratio between trifluoroethylene and HCl may be adjusted to the desired value by conventional means.

Thus, in a first preferred aspect, the process for making the composition of the invention comprises the steps of: preparing a gaseous composition comprising trifluoroethylene and HCl by the gas-phase catalytic hydrodechlorination of chlorotrifluoroethylene in the presence of hydrogen; optionally adjusting the molar ratio trifluoroethylene:HCl to be in the range from 10:90 to 63:37, preferably from 40:60 to 60:40; and compressing said gaseous composition to obtain a liquid or a compressed gas at a pressure from 0.50 MPa to 5.00 MPa.

An alternative gas-phase catalytic process for the preparation of trifluoroethylene is known, wherein 1,1,2-trichloro-1,2,2-trifluoroethane and hydrogen are reacted in the gas-phase in the presence of a heterogeneous catalyst, see for instance EP 459463 A (DAIKIN INDUSTRIES LIMITED) Apr. 12, 1991. The process provides trifluoroethylene and HCl as a by-product in a theoretical molar ratio of 25:75. The process is typically carried out at atmospheric pressure thus the effluent gas, after a purification step to remove any unreacted reagents as well as by-products, has to be compressed in order to provide the inventive composition. The amount of HCl in the composition may optionally be adjusted, for instance by partial removal of HCl to increase the ratio of trifluoroethylene, with conventional means known in the art.

Thus, in a second preferred aspect, the process for making the composition of the invention comprises the steps of: preparing a gaseous composition comprising trifluoroethylene and HCl by the gas-phase catalytic hydrodechlorination of 1,1,2-trichloro-1,2,2-trifluoroethane in the presence of hydrogen; optionally adjusting the molar ratio trifluoroethylene:HCl to be in the range from 10:90 to 63:37, preferably from 25:75 to 60:40; and compressing said gaseous composition to obtain a liquid or a compressed gas at a pressure from 0.50 MPa to 5.00 MPa.

A third object of the present invention is a process of storing or transporting the composition of the first object comprising the step of maintaining the composition in the liquid phase or in the compressed gas phase at a pressure of from 0.50 to 5.00 MPa, optionally at a temperature below ambient. The partial pressure of trifluoroethylene preferably does not exceed 2.50 MPa.

The term "storage" is used herein to indicate storing the composition for any length of time, from a short period, e.g. minutes or hours, to long periods, e.g. weeks or months.

In the context of the present invention the term transportation refers to any type of transportation, from a short distance, e.g. within the same chemical plant from one piece of equipment to another, to a long distance, e.g. from one geographical location to another.

Storage and transportation can be done in any type of suitable container. Accordingly, a further object of the present invention is a container containing the composition of the first object.

The container may have a variety of forms and functions. It can be a storage tank or a transportable container, such as a cylinder, a tank truck, a railway tank car or the like. The container can also be a pipe, for instance a pipe connecting any part of a chemical plant to another. The container may also be any chemical reaction or processing equipment.

The container should be made in a material suitable for contact with HCl; additionally the container should be constructed in a suitable way to resist to the pressures required by the invention. These requirements are well known to a person skilled in the art of the safe handling of corrosive and explosive materials.

The definitions and preferences defined previously within the context of the inventive composition apply to the process for preparing the composition, to the process for storing and transporting the composition as well as to the container containing said composition.

The present invention will now be described in more details by reference to the following examples, whose purposes are merely illustrative and do not limit the scope of the invention.

Should the disclosure of any of the patents, patent applications, and publications that are incorporated herein by reference conflict with the present description to the extent that it might render a term unclear, the present description shall take precedence.

EXAMPLES

Test Methodologies

Tests with gaseous compositions were carried out according to European standard EN 1839 "Determination of the explosion limits of gases and vapours" using a 3 dm$^3$ pressure resistant stainless steel vessel equipped with a piezoresistive pressure transducer, type KELLER PA-10, measuring range 0 MPa to 10 MPa, and a temperature recording detector. The transducer recorded the initial pressure ($p_i$) as well as the pressure-time-histories after ignition.

The reactivity of liquid compositions was tested according to an amendment to Chapter 2.2 "Flammable gases" of the UN Globally Harmonized System of Classification and Labelling of Chemicals (GHS, Forth Revised Edition; UN Documents "ST/SG/AC.10/C.4/2010/9" and "ST/SG/AC.10/C.4/2010/10"). The test substance was filled to 1 dm$^3$ pressure resistant test vessel, equipped with an ignition source located approx. 5 mm above the surface of the liquid.

The ignition source in both types of tests was a fusing (exploding) wire igniter which was located in the center of the vessel. The igniter consisted of two insulated electrodes at 5 mm distance, holding a nickeline wire of 0.12 mm diameter on its ends. The wire melted and then an electrical arc burned between the electrodes for a time extending in maximum to half a period of the supply voltage (0.01 s). A burning time of 3.8 ms was selected for the tests, corresponding to an ignition energy of about 15 J to 23 J which covers almost 90% of all existing ignition sources.

The safety characteristics and terms used in the following examples are defined as follows:

Initial Pressure (pi): the pressure in the closed explosion vessel before ignition.

Explosion Pressure (pex): the maximum value of the pressure, which arises after the ignition due to the reaction in the closed explosion vessel.

Explosion Pressure Ratio (pex/pi): the explosion pressure ratio is used as ignition criterion. If $p_{ex}/p_i > 1.1$ the reaction was defined as explosion.

Pressure Limit of Stability for Pure Trifluoroethylene in the Gas Phase and Stability of Liquid Trifluoroethylene Trifluoroethylene was fed to the evacuated ignition vessel to reach the initial test pressure.

After about 30 s the quiescent gas phase was ignited and the pressure-time-histories recorded. The initial pressure was varied in steps of 0.05 MPa till the highest pressure was determined at which no explosion according to the defined ignition criterion ($p_{ex}/p_i > 1.1$) occurred. This pressure limit was found to be 0.40 MPa. It was validated by further two ignitions, the value in Table 1 is an average of the three repetitions.

TABLE 1

| initial pressure $p_i$ (MPa) | explosion pressure $p_{ex}$ (MPa) | $p_{ex}/p_i$ |
|---|---|---|
| 0.40 | 0.42 | 1.05 |
| 0.50 | 0.76 | 1.53 |
| 0.55 | 5.95 | 10.82 |
| 0.60 | 5.82 | 9.70 |

If a chemically unstable gas like trifluoroethylene is liquefied the question arise if that liquid phase is also able to deflagrate if an ignition is present. Therefore a further test was carried out in a 1 dm$^3$ vessel containing 200 ml of liquefied trifluoroethylene at a temperature of 20° C. The corresponding vapour pressure at this temperature was 1.98 MPa. After ignition a pressure increase was detected. The initial pressure in the system was more than three times higher than the pressure limit of stability of 0.40 MPa when the safety pressure release of the equipment released the pressure. Due to the extreme pressure increase recorded in the system it can be concluded that decomposition at the surface of the liquid phase started directly after ignition. Due to the heat release liquid trifluoroethylene was vaporized and further fed the decomposition at the surface.

Example 1

Stability of Trifluoroethylene/HCl Compositions

Mixtures of trifluoroethylene and HCl were prepared directly in the ignition vessel by using a nozzle pipe. First trifluoroethylene was fed to the evacuated ignition vessel up to the partial pressure corresponding to the desired molar ratio of the composition to be tested at the desired initial pressure. Then HCl was filled directly from the gas cylinder up to the initial pressure. After about 30 s the quiescent gas phase was ignited and the pressure-time-histories were recorded. The initial temperature was 25° C. for the tests up to 3.00 MPa. The tests at 5.00 MPa were carried out at 45° C. The results are reported in Table 2.

TABLE 2

| Run # | Composition | | initial pressure $p_i$ (MPa) | explosion pressure $p_{ex}$ (MPa) | $p_{ex}/p_i$ |
|---|---|---|---|---|---|
| | trifluoroethylene (mol %) | HCl (mol %) | | | |
| 1 | 25 | 75 | 1.80 | 1.81 | 1.01 |
| 2 | 39 | 61 | 1.85 | 1.86 | 1.01 |
| 3 | 50 | 50 | 1.82 | 1.83 | 1.01 |
| 4 | 50 | 50 | 3.05 | 3.05 | 1.00 |
| 5 | 50 | 50 | 5.06 | 5.10 | 1.01 |
| 6 | 60 | 40 | 1.81 | 1.83 | 1.01 |
| 7 | 61 | 39 | 1.88 | 1.93 | 1.03 |
| 8 | 62 | 38 | 1.76 | 1.90 | 1.08 |
| 9 | 63 | 37 | 1.80 | 1.83 | 1.01 |

The data in Table 2 show the increased stability of the inventive compositions with respect to pure trifluoroethylene. Compositions containing the lowest amount of HCl, those wherein the ratio trifluoroethylene/HCl is 63:37, are stable up to a pressure which is at least 4 times higher than the maximum stability pressure of pure trifluoroethylene (1.80 MPa vs. 0.40).

Example 2

Determination of the Stability of the Gas Phase in Equilibrium with a Liquid Trifluoroethylene/HCl Composition Having a 50:50 Molar Ratio The stability of the gas phase in equilibrium with a liquid composition of trifluoroethylene and HCl in a 50:50 molar ratio was tested by partially filling a reservoir with the liquid and sequentially withdrawing, and testing according to the general procedure, the gas in the head space of the vessel. For each test the gas in the head space was charged into the ignition vessel for carrying out the ignition test. Initial load of the reservoir was about 70% of the total volume of 1 L. The mole fractions of trifluoroethylene and HCl in the head space varied from experiment to experiment. Since the vapour pressure of HCl is much higher than that of trifluoroethylene it can be assumed that the mole fraction of trifluoroethylene was less than 50% in the first experiment and increased from experiment to experiment. Thus an ignition became more likely from experiment to experiment. The experiment showed that at least down to 80-85% of the initial charge the gas phase in the head space was not flammable. This is important information to determine the safety of operations like the discharge of a liquid composition from a reservoir.

The invention claimed is:

1. A liquid or compressed gas composition comprising trifluoroethylene and hydrogen chloride (HCl) in a molar ratio of trifluoroethylene:HCl from 10:90 to 63:37, wherein when the composition is a compressed gas the pressure is from 0.50 to 5.00 MPa.

2. The composition according to claim 1, wherein the composition is a liquid composition.

3. The composition according to claim 2, wherein the molar ratio of trifluoroethylene:HCl is no more than 50:50.

4. The composition according to claim 2, wherein the composition comprises at least 20% by weight of the combined weight of trifluoroethylene and HCl.

5. The composition according to claim 1, wherein the composition is a compressed composition.

6. The composition according to claim 5, wherein the molar ratio of trifluoroethylene:HCl is from 40:60 to 60:40.

7. The composition according to claim 5, wherein the composition comprises at least 50% by weight of the combined weight of trifluoroethylene and HCl.

8. The composition according to claim 5, wherein the composition has a pressure of from 0.50 to 2.00 MPa, wherein the composition comprises at least 95% by weight of the combined weight of trifluoroethylene and HCl, and wherein the molar ratio of trifluoroethylene:HCl is from 50:50 to 60:40.

9. The composition according to claim 5, wherein the composition has a pressure of from 0.50 to 5.00 MPa, wherein the composition comprises at least 95% by weight of the combined weight of trifluoroethylene and HCl, and wherein the molar ratio of trifluoroethylene:HCl is from 40:60 to 50:50.

10. A process for the preparation of the composition of claim 1, the process comprising compressing a gaseous composition comprising trifluoroethylene and HCl in a molar ratio from 10:90 to 63:37 to obtain a liquid or a compressed gas at a pressure from 0.50 MPa to 5.00 MPa.

11. The process according to claim 10, wherein the gaseous composition is prepared by mixing gaseous trifluoroethylene and gaseous HCl at a pressure of less than 0.50 MPa.

12. The process according to claim 10, wherein the gaseous composition is prepared by the gas-phase catalytic hydrodechlorination of chlorotrifluoroethylene in the presence of hydrogen.

13. The process according to claim 10, wherein the gaseous composition is prepared by the gas-phase catalytic hydrodechlorination of 1,1,2-trichloro-1,2,2-trifluoroethane in the presence of hydrogen.

14. A process for storing or transporting the composition of claim 1, the process comprising maintaining the composition in the liquid phase or in the compressed gas phase at a pressure of from 0.50 to 5.00 MPa.

15. The process according to claim 11 wherein the gaseous composition is prepared by mixing gaseous trifluoroethylene and gaseous HCl at atmospheric pressure.

* * * * *